(12) United States Patent
Baker et al.

(10) Patent No.: US 12,127,958 B2
(45) Date of Patent: Oct. 29, 2024

(54) INTRALUMINAL DEVICE AND METHOD WITH ANTI-MIGRATION

(71) Applicant: BFKW, LLC, Ada, MI (US)

(72) Inventors: Randal S. Baker, Grand Rapids, MI (US); Frederick J. Walburn, Ada, MI (US)

(73) Assignee: BFKW, LLC, Ada, MI (US)

( * ) Notice: Subject to any disclaimer, the term of this patent is extended or adjusted under 35 U.S.C. 154(b) by 504 days.

(21) Appl. No.: 17/484,344

(22) Filed: Sep. 24, 2021

(65) Prior Publication Data
US 2022/0039977 A1    Feb. 10, 2022

Related U.S. Application Data

(63) Continuation-in-part of application No. PCT/IB2020/052765, filed on Mar. 24, 2020.

(60) Provisional application No. 62/823,259, filed on Mar. 25, 2019, provisional application No. 63/226,257, filed on Jul. 28, 2021.

(51) Int. Cl.
*A61F 2/90* (2013.01)
*A61F 2/04* (2013.01)

(52) U.S. Cl.
CPC .......... *A61F 2/90* (2013.01); *A61F 2/04* (2013.01); *A61F 2002/044* (2013.01); *A61F 2220/0016* (2013.01); *A61F 2230/0052* (2013.01); *A61F 2250/0039* (2013.01)

(58) Field of Classification Search
CPC ........ A61F 2/04; A61F 2/90; A61F 2002/044; A61F 2002/045; A61F 2250/0039; A61F 2220/0016; A61F 2230/0052
See application file for complete search history.

(56) References Cited

U.S. PATENT DOCUMENTS

| | | | |
|---|---|---|---|
| 4,403,604 A | 9/1983 | Wilkinson et al. |
| 4,607,618 A | 8/1986 | Angelchik |
| 5,234,454 A | 8/1993 | Bangs |
| 5,306,300 A | 4/1994 | Berry |

(Continued)

FOREIGN PATENT DOCUMENTS

| | | | |
|---|---|---|---|
| CN | 108938163 A | 12/2018 |
| EP | 0760696 B1 | 8/2001 |

(Continued)

OTHER PUBLICATIONS

"Obesity: Super-Sized Medical Device Market", Start-Up, Mar. 2003, Technology Strategies (Long Article), pp. 1-10 and a cover page.

(Continued)

*Primary Examiner* — Dinah Baria
(74) *Attorney, Agent, or Firm* — Gardner, Linn, Burkhart & Ondersma LLP

(57) ABSTRACT

An intraluminal device and method of resisting migration of a device in a lumen, the lumen having muscle defining an intraluminal sphincter includes a device having a body with a size and shape of a portion of the lumen. The device further includes at least one tine extending distally from the body. The at least one tine is rigid or semi rigid. The device is deployed in the lumen with the body proximal the sphincter with respect to peristaltic movement of the lumen and with the at least one tine penetrating the muscle of the sphincter to resist distal migration.

21 Claims, 15 Drawing Sheets

(56) References Cited

U.S. PATENT DOCUMENTS

| | | |
|---|---|---|
| 5,366,504 A | 11/1994 | Andersen et al. |
| 5,507,755 A | 4/1996 | Gresl et al. |
| 5,662,713 A | 9/1997 | Andersen et al. |
| 5,741,279 A | 4/1998 | Gordon et al. |
| 5,820,584 A | 10/1998 | Crabb |
| 6,146,416 A | 11/2000 | Andersen et al. |
| 6,264,700 B1 | 7/2001 | Kilcoyne et al. |
| 6,280,415 B1 | 8/2001 | Johnson |
| 6,312,437 B1 | 11/2001 | Kortenbach |
| 6,355,070 B1 | 3/2002 | Andersen et al. |
| 6,398,802 B1 | 6/2002 | Yee |
| 6,432,040 B1 | 8/2002 | Meah |
| 6,447,533 B1 | 9/2002 | Adams |
| 6,468,298 B1 | 10/2002 | Pelton |
| 6,544,291 B2 | 4/2003 | Taylor |
| 6,558,400 B2 | 5/2003 | Deem et al. |
| 6,572,627 B2 | 6/2003 | Gabbay |
| 6,656,194 B1 | 12/2003 | Gannoe et al. |
| 6,675,809 B2 | 1/2004 | Stack et al. |
| 6,736,828 B1 | 5/2004 | Adams et al. |
| 6,740,121 B2 | 5/2004 | Geitz |
| 6,746,460 B2 | 6/2004 | Gannoe et al. |
| 6,755,869 B2 | 6/2004 | Geitz |
| 6,773,440 B2 | 8/2004 | Gannoe et al. |
| 6,800,081 B2 | 10/2004 | Parodi |
| 6,802,868 B2 | 10/2004 | Silverman et al. |
| 6,845,776 B2 | 1/2005 | Stack et al. |
| 6,916,332 B2 | 7/2005 | Adams |
| 6,960,233 B1 | 11/2005 | Berg et al. |
| 6,981,978 B2 | 1/2006 | Gannoe |
| 6,994,095 B2 | 2/2006 | Burnett |
| 6,994,715 B2 | 2/2006 | Gannoe et al. |
| 7,025,791 B2 | 4/2006 | Levine et al. |
| 7,033,373 B2 | 4/2006 | de la Torre et al. |
| 7,033,384 B2 | 4/2006 | Gannoe et al. |
| 7,037,344 B2 | 5/2006 | Kagan et al. |
| 7,044,979 B2 | 5/2006 | Silverman et al. |
| 7,066,945 B2 | 6/2006 | Hashiba et al. |
| 7,083,629 B2 | 8/2006 | Weller et al. |
| 7,083,630 B2 | 8/2006 | DeVries et al. |
| 7,087,088 B2 | 8/2006 | Berg et al. |
| 7,097,650 B2 | 8/2006 | Weller et al. |
| 7,097,665 B2 | 8/2006 | Stack et al. |
| 7,111,627 B2 | 9/2006 | Stack et al. |
| 7,146,984 B2 | 12/2006 | Stack et al. |
| 7,152,607 B2 | 12/2006 | Stack et al. |
| 7,167,750 B2 | 1/2007 | Knudson et al. |
| 7,211,114 B2 | 5/2007 | Bessler et al. |
| 7,220,284 B2 | 5/2007 | Kagan et al. |
| 7,232,461 B2 | 6/2007 | Ramer |
| 7,347,875 B2 | 3/2008 | Levine et al. |
| 7,431,725 B2 | 10/2008 | Stack et al. |
| 7,445,010 B2 | 11/2008 | Kugler et al. |
| 7,449,024 B2 | 11/2008 | Stafford |
| 7,678,068 B2 | 3/2010 | Levine et al. |
| 7,682,330 B2 | 3/2010 | Meade et al. |
| 7,704,264 B2 | 4/2010 | Ewers et al. |
| 7,708,752 B2 | 5/2010 | Durgin |
| 7,753,870 B2 | 7/2010 | Demarais et al. |
| 7,771,382 B2 | 8/2010 | Levine et al. |
| 7,794,447 B2 | 9/2010 | Dann et al. |
| 7,815,589 B2 | 10/2010 | Meade et al. |
| 7,815,591 B2 | 10/2010 | Levine et al. |
| 7,828,839 B2 * | 11/2010 | Cook ................ A61F 2/848 623/1.36 |
| 7,846,174 B2 | 12/2010 | Baker et al. |
| 7,922,650 B2 | 4/2011 | McWeeney et al. |
| 7,976,488 B2 | 7/2011 | Levine et al. |
| 7,981,163 B2 | 7/2011 | Meade et al. |
| 8,029,455 B2 | 10/2011 | Stack et al. |
| 8,043,355 B2 | 10/2011 | Shin et al. |
| 8,100,931 B2 | 1/2012 | Baker et al. |
| 8,137,301 B2 | 3/2012 | Levine et al. |
| 8,142,513 B2 | 3/2012 | Shalon et al. |
| 8,162,871 B2 | 4/2012 | Levine et al. |
| 8,252,009 B2 | 8/2012 | Weller |
| 8,282,598 B2 | 10/2012 | Belhe et al. |
| 8,372,087 B2 | 2/2013 | Baker et al. |
| 8,447,403 B2 | 5/2013 | Sharma et al. |
| 8,506,477 B2 | 8/2013 | Waller et al. |
| 8,529,431 B2 | 9/2013 | Baker et al. |
| 8,556,956 B2 | 10/2013 | Cully et al. |
| 8,672,831 B2 | 3/2014 | Baker et al. |
| 8,721,528 B2 | 5/2014 | Ho et al. |
| 8,778,011 B2 | 7/2014 | Ryan |
| 8,784,436 B2 | 7/2014 | Ho et al. |
| 8,801,599 B2 | 8/2014 | Baker et al. |
| 8,894,670 B2 | 11/2014 | Baker et al. |
| 9,055,998 B2 | 6/2015 | Baker |
| 9,060,844 B2 | 6/2015 | Kagan et al. |
| 9,107,742 B2 | 8/2015 | Cully et al. |
| 9,198,789 B2 | 12/2015 | Baker et al. |
| 9,375,338 B2 | 6/2016 | Baker et al. |
| 9,414,948 B2 | 8/2016 | Baker et al. |
| 9,545,326 B2 | 1/2017 | Baker et al. |
| 9,549,833 B2 | 1/2017 | McHugo |
| 9,629,733 B2 | 4/2017 | Roeder |
| 9,839,545 B2 | 12/2017 | Baker et al. |
| 9,872,787 B2 | 1/2018 | Baker et al. |
| 10,182,901 B2 | 1/2019 | Baker et al. |
| 10,271,940 B2 | 4/2019 | Baker et al. |
| 10,682,219 B2 | 6/2020 | Foote et al. |
| 10,687,933 B2 | 6/2020 | Baker et al. |
| 10,786,380 B2 | 9/2020 | Baker et al. |
| 10,792,174 B2 | 10/2020 | Baker et al. |
| 11,013,629 B2 | 5/2021 | Baker |
| 11,020,213 B2 | 6/2021 | Foote et al. |
| 11,129,703 B2 | 9/2021 | Baker et al. |
| 2001/0011543 A1 | 8/2001 | Forsell |
| 2001/0020189 A1 | 9/2001 | Taylor |
| 2002/0032487 A1 | 3/2002 | Dua et al. |
| 2002/0091395 A1 | 7/2002 | Gabbay |
| 2003/0040804 A1 | 2/2003 | Stack et al. |
| 2003/0040808 A1 | 2/2003 | Stack et al. |
| 2003/0065359 A1 | 4/2003 | Weller et al. |
| 2003/0109935 A1 | 6/2003 | Geitz |
| 2003/0199989 A1 | 10/2003 | Stack et al. |
| 2003/0212450 A1 | 11/2003 | Schlick |
| 2004/0044357 A1 | 3/2004 | Gannoe et al. |
| 2004/0087976 A1 | 5/2004 | DeVries et al. |
| 2004/0092892 A1 | 5/2004 | Kagan et al. |
| 2004/0106987 A1 | 6/2004 | Palasis et al. |
| 2004/0116999 A1 | 6/2004 | Ledergerber |
| 2004/0117031 A1 | 6/2004 | Stack et al. |
| 2004/0122456 A1 | 6/2004 | Vahid |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0172141 A1 | 9/2004 | Stack et al. |
| 2004/0210111 A1 | 10/2004 | Okada |
| 2004/0220682 A1 | 11/2004 | Levine et al. |
| 2005/0004582 A1 | 1/2005 | Edoga et al. |
| 2005/0043683 A1 | 2/2005 | Ravo |
| 2005/0080395 A1 | 4/2005 | Levine et al. |
| 2005/0096728 A1 | 5/2005 | Ramer |
| 2005/0125020 A1 | 6/2005 | Meade et al. |
| 2005/0177181 A1 | 8/2005 | Kagan |
| 2005/0192599 A1 | 9/2005 | Demarais |
| 2005/0192629 A1 | 9/2005 | Saadat et al. |
| 2005/0197715 A1 | 9/2005 | Kugler et al. |
| 2005/0228504 A1 | 10/2005 | Demarais |
| 2005/0245788 A1 | 11/2005 | Gerber |
| 2005/0245957 A1 | 11/2005 | Starkebaum et al. |
| 2005/0247320 A1 | 11/2005 | Stack et al. |
| 2005/0251165 A1 | 11/2005 | Vaughan et al. |
| 2005/0251176 A1 | 11/2005 | Swanstrom et al. |
| 2005/0283235 A1 | 12/2005 | Kugler et al. |
| 2006/0020277 A1 | 1/2006 | Gostout et al. |
| 2006/0036293 A1 | 2/2006 | Whitehurst et al. |
| 2006/0064120 A1 | 3/2006 | Levine et al. |
| 2006/0074473 A1 | 4/2006 | Gertner |
| 2006/0089571 A1 | 4/2006 | Gertner |
| 2006/0142844 A1 | 6/2006 | Lowe et al. |
| 2006/0149307 A1 | 7/2006 | Durgin |

(56) References Cited

U.S. PATENT DOCUMENTS

| | | |
|---|---|---|
| 2006/0155375 A1 | 7/2006 | Kagan et al. |
| 2006/0161139 A1 | 7/2006 | Levine et al. |
| 2006/0190019 A1 | 8/2006 | Gannoe et al. |
| 2006/0247721 A1 | 11/2006 | Maschino et al. |
| 2006/0253131 A1 | 11/2006 | Wolniewicz, III |
| 2006/0253142 A1 | 11/2006 | Bjerken |
| 2006/0253191 A1 | 11/2006 | Salahieh et al. |
| 2006/0264699 A1 | 11/2006 | Gertner |
| 2006/0265082 A1 | 11/2006 | Meade et al. |
| 2007/0005147 A1 | 1/2007 | Levine et al. |
| 2007/0010866 A1 | 1/2007 | Dann et al. |
| 2007/0010875 A1 | 1/2007 | Trout et al. |
| 2007/0088428 A1 | 4/2007 | Teichman |
| 2007/0112409 A1 | 5/2007 | Wu et al. |
| 2007/0123994 A1 | 5/2007 | Ortiz et al. |
| 2007/0166396 A1 | 7/2007 | Badylak et al. |
| 2007/0179590 A1 | 8/2007 | Lu et al. |
| 2007/0198035 A1 | 8/2007 | Threlkeld |
| 2007/0208429 A1 | 9/2007 | Leahy |
| 2007/0233221 A1 | 10/2007 | Raju |
| 2007/0260112 A1 | 11/2007 | Rahmani |
| 2007/0270742 A1 | 11/2007 | Guetty |
| 2007/0276432 A1 | 11/2007 | Stack et al. |
| 2007/0293716 A1 | 12/2007 | Baker et al. |
| 2008/0015523 A1 | 1/2008 | Baker |
| 2008/0015618 A1 | 1/2008 | Sonnenschein et al. |
| 2008/0015633 A1 | 1/2008 | Abbott et al. |
| 2008/0065122 A1 | 3/2008 | Stack et al. |
| 2008/0065136 A1 | 3/2008 | Young |
| 2008/0215076 A1 | 9/2008 | Baker |
| 2008/0312678 A1 | 12/2008 | Pasricha |
| 2009/0018389 A1 | 1/2009 | Laufer et al. |
| 2009/0138071 A1 | 5/2009 | Cheng et al. |
| 2009/0177215 A1 | 7/2009 | Stack et al. |
| 2009/0187230 A1 | 7/2009 | Dilorenzo |
| 2009/0240340 A1 | 9/2009 | Levine et al. |
| 2009/0248171 A1 | 10/2009 | Levine et al. |
| 2009/0270818 A1 | 10/2009 | Duke |
| 2010/0010298 A1 | 1/2010 | Bakos et al. |
| 2010/0030017 A1 | 2/2010 | Baker et al. |
| 2010/0114124 A1 | 5/2010 | Kelleher et al. |
| 2010/0114130 A1 | 5/2010 | Meade et al. |
| 2010/0256775 A1 | 10/2010 | Belhe et al. |
| 2010/0280313 A1 | 11/2010 | Gasche et al. |
| 2010/0305590 A1 | 12/2010 | Holmes et al. |
| 2011/0004146 A1 | 1/2011 | Priplata et al. |
| 2011/0009690 A1 | 1/2011 | Belhe et al. |
| 2011/0264234 A1 | 10/2011 | Baker et al. |
| 2012/0053653 A1 | 3/2012 | Hiernaux et al. |
| 2012/0083783 A1 | 4/2012 | Ryan |
| 2012/0095497 A1 | 4/2012 | Babkes et al. |
| 2012/0191213 A1 | 7/2012 | Baker et al. |
| 2012/0191215 A1 | 7/2012 | Baker et al. |
| 2012/0203061 A1 | 8/2012 | Birk |
| 2012/0310327 A1 | 12/2012 | McHugo |
| 2013/0123811 A1 | 5/2013 | Baker et al. |
| 2013/0296913 A1 | 11/2013 | Foote et al. |
| 2013/0324902 A1 | 12/2013 | Miller et al. |
| 2014/0135799 A1 | 5/2014 | Henderson |
| 2014/0158747 A1 | 6/2014 | Measamer et al. |
| 2014/0277341 A1 | 9/2014 | Havel et al. |
| 2015/0039092 A1 | 2/2015 | Baker et al. |
| 2015/0182239 A1 | 7/2015 | Baker et al. |
| 2016/0151233 A1 | 6/2016 | Baker et al. |
| 2016/0228268 A1 | 8/2016 | Hingston et al. |
| 2017/0172723 A1 | 6/2017 | Foote et al. |
| 2017/0360550 A1* | 12/2017 | Foote ............... A61F 5/0089 |
| 2018/0104080 A1 | 4/2018 | Baker et al. |
| 2019/0298560 A1 | 10/2019 | Belhe et al. |

FOREIGN PATENT DOCUMENTS

| | | |
|---|---|---|
| EP | 1808888 A2 | 7/2007 |
| EP | 2240215 B1 | 1/2014 |
| JP | 2660101 | 6/1997 |
| JP | 2006-103873 A | 4/2006 |
| JP | 2007508053 A | 4/2007 |
| JP | 2011509758 A | 3/2011 |
| RU | 2045233 C1 | 10/1995 |
| RU | 94026119 A | 8/1996 |
| RU | 2386455 | 4/2010 |
| WO | WO 93/22986 | 11/1993 |
| WO | WO 94/12136 | 6/1994 |
| WO | WO 01/35834 A1 | 5/2001 |
| WO | WO 01/85034 A1 | 11/2001 |
| WO | WO 02/060328 A1 | 8/2002 |
| WO | WO 02/094105 A2 | 11/2002 |
| WO | WO 2004/019826 A1 | 3/2004 |
| WO | WO 2004/064680 A1 | 8/2004 |
| WO | WO 2004/064685 | 8/2004 |
| WO | WO 2005/037152 A1 | 4/2005 |
| WO | WO 2006/044640 A1 | 4/2006 |
| WO | WO 2006/078672 A1 | 7/2006 |
| WO | WO 2007/092390 A2 | 8/2007 |
| WO | WO 2008/100984 A2 | 8/2008 |
| WO | WO 2008/101048 A2 | 8/2008 |
| WO | WO 2008/101078 A2 | 8/2008 |
| WO | WO 2009/048398 A1 | 4/2009 |
| WO | WO 2009/091899 A2 | 7/2009 |
| WO | WO 2010/117641 A2 | 10/2010 |
| WO | WO 2011/056608 A1 | 5/2011 |
| WO | WO 2011/063307 A1 | 5/2011 |
| WO | WO 2011/089601 A1 | 7/2011 |
| WO | WO 2011/097209 A1 | 8/2011 |
| WO | WO 2011/116025 A1 | 9/2011 |
| WO | WO 2012/044917 A1 | 4/2012 |
| WO | WO 2012/136249 A1 | 10/2012 |
| WO | WO 2012/162114 A1 | 11/2012 |
| WO | WO 2013/090190 A1 | 6/2013 |
| WO | WO 2013/134227 A1 | 9/2013 |
| WO | WO 2014/141239 A1 | 9/2014 |
| WO | WO 2015/031077 A1 | 3/2015 |
| WO | WO 2016/109346 A1 | 7/2016 |
| WO | WO 2018/073752 A1 | 4/2018 |
| WO | WO 2018/083632 A1 | 5/2018 |

OTHER PUBLICATIONS

Andrew S. Lowe, M.D. and Maria B. Sheridan, M.D., "Esphogeal Stenting", Seminars in Interventional Radiology, vol. 21, No. 3, 2004, pp. 157-166.

"Polyflex® Espohageal Stent", Silicone Covered Stent, Boston Scientific, three pages (2003).

Andrew F.R. Dixon, Johgn B. Dixon, and Paul E. O'Brien, "Laparoscopic Adjustable Gastric Banding Induces Prolonged Satiety: A Randomized Blind Crossover Study", The Journal of Clinical Endocrinology & Metabolism, pp. 813-819, 2005.

Roman, S. et al., "Intragastric balloon for 'non-morbid' obesity: a retrospective evaluation of tolerance and efficacy," Obes. Surg., 2004, 14(4), 539-44, abstract, [on-line], [found Apr. 17, 2009, from Pubmed database].

Busetto, L. et al., "Preoperative weight loss by intragastric balloon in super-obese patients treated with laparoscopic gastric banding: a case-control study," Obes Surg., 2004, 14(5), 671-6, abstract, [online], [found Apr. 17, 2009, from Pubmed database].

Summary of Official Action dated Oct. 29, 2009, from the Israel Patent Office in a patent application corresponding to the present application.

Lowe, Andrew S., M.D. and Sheridan, Maria B., M.D., "Esophageal Stenting," annotated by Israel Patent Office (2004).

Abstract and claims of U.S. Pat. No. 6,960,233 annotated by the Israel Patent Office (Nov. 1, 2005).

Schembre, Drew, "Advances in Esophageal Stenting: the Evolution of Fully Covered Stents for Malignant and Benign Disease," Adv. Ther., Springer Healthcare, Apr. 1, 2010, p. 1-13.

S. Fukudo, T. Nomura, M. Hongo, "Impact of corticotropin-releasing hormone on gastrointestinal motility and adrenocorticotropic hormone in normal controls and patients with irritable bowel syndrome", Jan. 19, 1998.

(56) References Cited

OTHER PUBLICATIONS

D.G. Maxton, D.F. Martin, P.J. Whorwell, M. Godfrey. "Abdominal distension in female patients with irritable bowel syndrome: exploration of possible mechanisms", Aug. 3, 1990.
Dixon et al. "Health Outcomes of Severely Obese Type 2 Diabetic Subjects 1 Year After Laparoscopic Adjustable Gastric Banding". 2002. Diabetic Care 25:358-363. (Year 2002).
International Search Report of the International Searching Authority from corresponding Patent Cooperation Treaty (PCT) Patent Application No. PCT/IB2020/052169, mailed Jul. 15, 2020.

* cited by examiner ved in the lumen. The device may be deployed by (i) compressing the body and the another body in a deployment device, (ii) positioning the deployment device at least partially distal of the sphincter and deploying the another body from the deployment device distal of the sphincter, (iii) moving the deployment device proximally and deploying the body and the at least one tine proximal the muscle of the sphincter and (iv) further deploying the device from the deployment device wherein the at least one tine subsequently penetrates the sphincter. The connector and/or another device may be sufficiently flexible in order to perform (iii) while maintaining said the other body generally distal to the sphincter.

INTRALUMINAL DEVICE AND METHOD WITH ANTI-MIGRATION

CROSS REFERENCE TO RELATED APPLICATIONS

The present application is a continuation-in-part of International patent application PCT/IB2020/052765 filed Mar. 24, 2020 which claims the benefit of U.S. provisional patent application 62/823,259 filed Mar. 25, 2019; the present application claims the benefit of U.S. provisional patent application 63/226,257 filed Jul. 28, 2021, the disclosures of which are hereby collectively incorporated herein by reference in their entirety.

BACKGROUND OF THE INVENTION

The present invention is directed to an intraluminal device such as a bariatric device or a metabolic disease treatment device and method of resisting distal migration of an intraluminal device in a lumen that experiences peristalsis.

Resisting migration in a lumen that experiences peristalsis is a difficult problem. In addition to migration distally in the direction of the peristalsis, migration can occur proximally in the opposite direction. For example, in the esophagus, the persistence of peristalsis presents a strong force tending to cause distal migration. Occasionally, proximal migration forces may be produced; for example, when the patient belches or vomits. Various techniques have been proposed to resist migration but were either ineffective, difficult to deploy or potentially injurious to the patient.

SUMMARY OF THE INVENTION

Peristalsis can result in significant variation in the diameter of a lumen between peaks and valleys of the peristaltic wave. This change in diameter is pronounced at muscular regions of the lumen that define sphincters. When attempting to resist distal migration of an intraluminal device deployed proximal to, or passing through, a sphincter, it is difficult resist distal migration of the device and not interfere with operation of the sphincter. The present invention provides a method of resisting migration of a device and an intraluminal device that is both robust and straightforward to deploy without the need for an additional deployment device. It can be used alone or in combination with other fixation techniques.

A method of resisting migration of a device in a lumen, the lumen having muscle defining an intraluminal sphincter, according to an aspect of the invention, includes a device having a body with a size and shape of a portion of the lumen. The device further includes at least one tine extending distally from the body. The at least one tine is rigid or semi rigid. The device is deployed in the lumen with the body proximal the sphincter with respect to peristaltic movement of the lumen, with the at least one tine penetrating the muscle of the sphincter.

The at least one tine may include at least two tines that are axially spaced around the body with respect to the lumen. The at least one tine may be configured to penetrate the sphincter muscle sufficiently to avoid detachment from the sphincter from the peristalsis of the lumen. The at least one tine may have a length from approximately 0.5 cm to approximately 2.0 cm.

The device body may be coupled with another body with a connector, with the other body being positioned distal of the sphincter and the connector passing through the sphincter with the device deployed in the lumen. The device may be deployed by (i) compressing the body and the another body in a deployment device, (ii) positioning the deployment device at least partially distal of the sphincter and deploying the another body from the deployment device distal of the sphincter, (iii) moving the deployment device proximally and deploying the body and the at least one tine proximal the muscle of the sphincter and (iv) further deploying the device from the deployment device wherein the at least one tine subsequently penetrates the sphincter. The connector and/or another device may be sufficiently flexible in order to perform (iii) while maintaining said the other body generally distal to the sphincter.

The body may be an esophageal member configured to the size and shape of the distal portion of the esophagus. The other body may be a cardiac member that is configured to the size and shape of a portion of the cardiac portion of the stomach and the connector passes through the esophageal-gastric (EG) sphincter.

The body may be configured to be positioned at the pylorus. The other body may be configured to the size and shape of a portion of the intestine and the connector passes through the pyloric sphincter. The at least one tine penetrates the pyloric sphincter.

The body may be configured to be positioned at the throat. The other body may be configured to the size and shape of a portion of the esophagus and the connector passes through the upper esophageal sphincter. The at least one tine penetrates the upper esophageal sphincter.

The body may be configured to be proximal the ileocecal valve, the other body may be configured to the size and shape of a portion of the large colon and the connector passes through the ileocecal valve. The at least one tine penetrates the sphincter of the ileocecal valve.

The at least one tine may be directed distally and outwardly but more distally than outwardly. The at least one tine may have a length of between approximately 0.5 cm and 2.0 cm. The angle between each tine and the central axis of the body may be between 5 degrees and approximately 45 degrees. An enlarged tip may be provided on the at least one tine to resist catching on a deployment device or other surface. The at least one tine may be configured to be retained entirely within the lumen and not penetrate the lumen.

An intraluminal device that is adapted to be deployed in a lumen that experiences peristaltic waves and has muscle defining an intraluminal sphincter, according to an aspect of the invention, includes a body having a size and shape of a portion of the lumen proximal of the sphincter and at least one tine extending distally from a distal portion of the body. The at least one tine is rigid or semi rigid. The at least one tine extends distally from the body with respect to peristaltic movement of the lumen and is adapted to penetrate the muscle of the sphincter when the body is deployed in the lumen proximal to the sphincter.

The at least one tine may be at least two tines that are axially spaced around with respect to the body. The at least one tine may have a length of at least a wavelength of a peristaltic wave of the lumen. The body may be coupled with another body using a connector. The other body has a size and shape to be deployed downstream of the sphincter and the connector being configured to pass through the sphincter.

The body may be an esophageal member that is configured to the size and shape of the distal portion of the esophagus and the other body a cardiac member that is configured to the size and shape of a portion of the cardiac portion of the stomach. The connector is adapted to pass through the esophageal-gastric (EG) sphincter and the at least one tine adapted to penetrate the EG sphincter.

The body may be configured to the size and shape of a portion of the pylorus and the other body configured to the size and shape of a portion of the intestine. The connector is adapted to pass through the pyloric sphincter and the at least one tine adapted to penetrate the pyloric sphincter.

The body may be configured to be positioned proximal the upper esophageal sphincter and the other body configured to the size and shape of a portion of the esophagus. The connector is adapted to pass through the upper esophageal sphincter and the at least one tine adapted to penetrate the upper esophageal sphincter.

The body may be configured to be positioned proximal the ileocecal valve and the other body configured to the size and shape of a portion of the large intestine. The connector is adapted to pass through the ileocecal valve and the at least one tine adapted to penetrate the sphincter of the ileocecal valve.

The at least one tine may be directed distally and outwardly but more distally than outwardly. The angle between each tine and the central axis of the body may be between 5 degrees and 45 degrees, such as between approximately 5 and approximately 30 degrees such as approximately 10 degrees. The at least one tine may have a length of between approximately 0.5 cm and approximately 2.0 cm.

An enlarged tip of the at least one tine to resist catching on a surface such as a deployment device. The at least one tine may be configured to be retained entirely within the lumen.

An intraluminal device that is adapted to be deployed in a lumen that experiences peristaltic waves and has muscle defining an intraluminal sphincter, according to an aspect of the invention, includes an esophageal member having a size and shape of a distal portion of the esophagus and at least one tine extending distally from a distal portion of the esophageal member. The at least one tine is rigid or semi-rigid. The at least one tine is adapted to penetrate the muscle of the EG sphincter when the esophageal member is deployed in the esophagus proximal to the gastro-esophageal sphincter. A cardiac member is coupled with said esophageal member with a connector. The connector is configured to cause the cardiac member to apply stress to the cardiac portion of the stomach when the connector passes through the gastro-esophageal sphincter and the cardiac member is in the stomach.

The at least one tine may be at least two tines that are axially spaced around the esophageal member. The at least one tine may be configured to penetrate the sphincter sufficiently to avoid separating from the sphincter by peristaltic effect on the device. The at least one tine may have a length of between approximately 0.5 cm and approximately 2.0 cm. The angle between each tine and the central axis of the esophageal member may be between approximately 5 degrees and approximately 45 degrees outwardly.

The connector and/or cardiac member may be sufficiently flexible in order to allow the esophageal member to be displaced proximally sufficiently to allow the at least one tine to engage the muscle of the gastro-esophageal sphincter. An enlarged tip may be provided on the least one tine to resist catching on a deployment device. The at least one tine is configured to be retained entirely within the lumen.

A method of resisting migration of a device in a lumen having muscle defining an intraluminal sphincter, according to an aspect of the invention, includes the device having a body with a size and shape of a portion of the lumen. The device further includes at least one tine extending outwardly and distally from the body. The at least one tine is rigid or semi rigid. The device is deployed in the lumen with the body proximal the sphincter with respect to peristaltic movement of the lumen with the at least one tine penetrating the muscle of the sphincter. The device is explanted by moving the at least one tine to not extend outwardly from the body.

The device may include a removal ring at a proximal end portion of the body and a retraction ring at a distal end portion of the body that is connected with the removal ring. Proximal force applied to the removal ring causes the retraction ring to move the at least one tine inwardly. The traction ring may move the at least one tine inwardly by a (i) reducing a diameter of the distal end portion of the body (ii), pulling inwardly on the at least one tine, and/or (iii) retracting the at least one tine into a pouch.

An intraluminal device and method of resisting distal migration of the intraluminal device deployed in a lumen that experiences peristaltic waves and has muscle defining an intraluminal sphincter, according to an aspect of the invention, includes the intraluminal device having a body having a size and shape of a portion of the lumen proximal of the sphincter and at least one anchor extending from the body and adapted to resist distal migration of the body. The at least one anchor includes a base extending distally from the body with respect to peristaltic movement of the lumen and at least one tine extending distally from the base. The base positions the at least one tine to penetrate the muscle of the sphincter when the body is deployed in the lumen proximal of the sphincter and the base allowing lateral motion of the tine with respect to the body in response to operation of the sphincter.

An intraluminal device and method of resisting distal migration of the intraluminal device deployed in a lumen that experiences peristaltic waves and has muscle defining an intraluminal sphincter, according to an aspect of the invention, includes the intraluminal device having an esophageal member having a size and shape of a portion of the distal portion of the esophagus, a cardiac member having a size and shape of the cardiac portion of the stomach coupled with said esophageal member with a connector. The connector is configured to cause the cardiac member to apply stress to the cardiac portion of the stomach when the connector passes through the EG sphincter and the cardiac member is in the stomach. At least one anchor extends distally from the esophageal member and resists distal migration of the esophageal member. The at least one anchor includes a base extending distally from the esophageal member and at least one tine extending distally from the base. The base positions the at least one tine to penetrate the muscle of the esophageal-gastric (EG) sphincter when the esophageal member is deployed in the esophagus upstream of the EG sphincter and allows lateral motion of the tine with respect to said esophageal member in response to operation of the EG sphincter.

The at least one anchor may be a plurality of said anchors distributed around a perimeter of the body. The at least one tine may have a length sufficient to penetrate to the muscularis of the sphincter without penetrating outside of the lumen. The at least one tine may be at least two tines. The at least two tines may be angular with respect to each other. The tine may include an enlarged diameter that is adapted to resist withdrawal of the at least one tine from the muscle of the sphincter. The enlarged diameter may be is shaped as a sphere or a triangle. The base may be pivotally mounted to the body. The body may include a mesh and a flexible cover over the mesh with the base being an extension of said mesh and flexible cover. The mesh may be a metal such as nitinol. The flexible cover may be a silicone.

In embodiments of the present invention the anchor is allowed to passively follow the diameter of the lower esophageal sphincter of the esopho-gastric junction responding to peristalsis while firmly resisting distal migration of the intraluminal device. Thus the invention provides anti-migration while responding passively to peristalsis.

These and other objects, advantages, purposes and features of this invention will become apparent upon review of the following specification in conjunction with the drawings.

DESCRIPTION OF THE PREFERRED EMBODIMENTS

Figure 1:
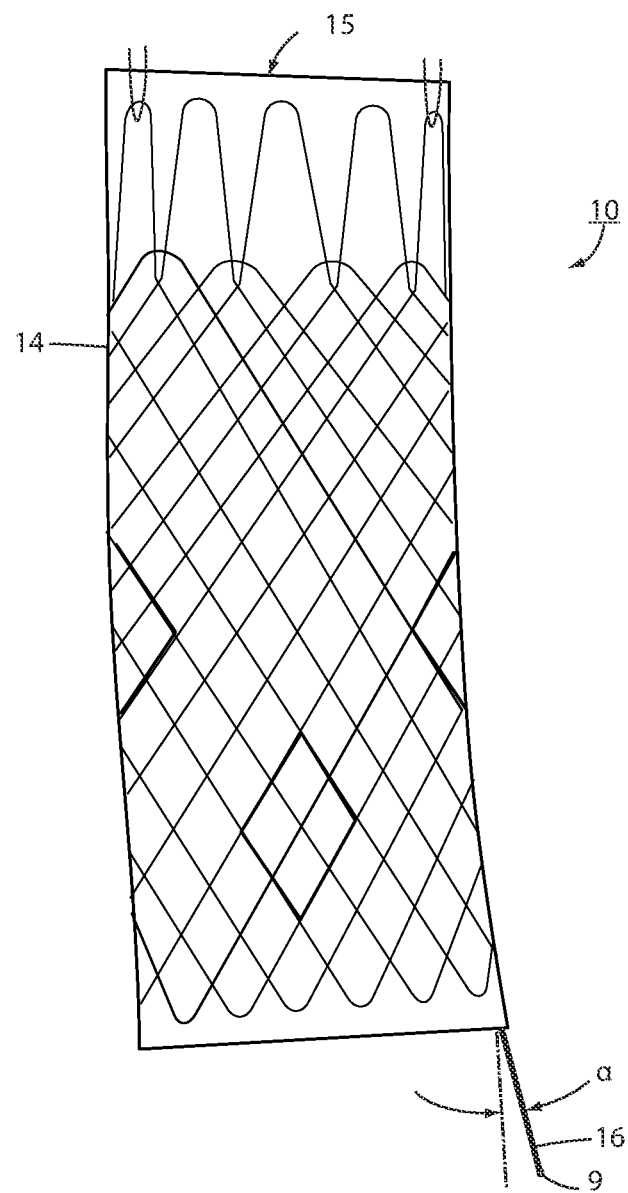
FIG. 1 is a side elevation of an intraluminal device according to an embodiment of the invention.
Figure 2:
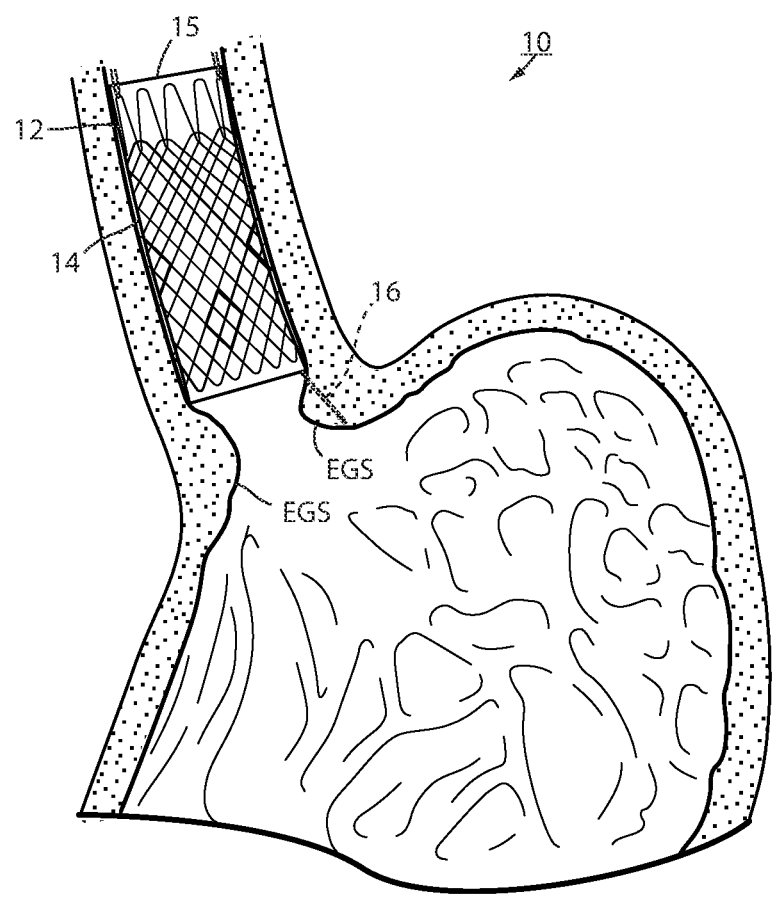
FIG. 2 is a view of the intraluminal device in FIG. 1 deployed to the GI tract of a recipient an positioned at the esophageal-gastric sphincter (ESP) of the recipient.

The present invention will now be described with reference to the accompanying figures, wherein the numbered elements in the following written description correspond to like-numbered elements in the figures.

Referring now to the drawings and the illustrative embodiments depicted therein, an intraluminal device 10 is adapted to be deployed in a lumen 12 that experiences peristaltic waves and has muscle defining an intraluminal sphincter or pseudo-sphincter, hereafter "sphincter". An example of such a lumen is a portion of the gastro-intestinal (GI) tract having sphincters including the upper esophageal sphincter (UES), the esophageal-gastric sphincter (EGS), the pyloric sphincter (PS) and the ileocecal valve (IV) that separates the large intestine from the small intestine. Intraluminal device 10 has a body 14 having a size and shape of a portion of the lumen proximal of the sphincter with respect to peristaltic movement of the lumen and a through opening 15 that allows movement of intraluminal content through the body. The through opening may be a central passage through the body or a shape of the body that allows intraluminal content to bypass the body.

Intraluminal device 10 further includes at least one tine 16. The at least one tine 16 extends distally from a distal portion of body 14 and is rigid or semi rigid. In this manner, with body 14 deployed in the lumen proximal the sphincter, the at least one tine 16 penetrates the muscle that defines the sphincter as peristalsis causes distal motion of the body thrusting the at least one tine distally. The penetration of the at least one tine in the sphincter is sufficient to resist action of peristalsis of lumen 12 separating the at least one tine from the sphincter. In this manner distal migration of body 14 is resisted even as the sphincter opens and closes. Thus the orientation of the at least one tine penetrating the sphincter resists distal migration of the body without placing excessive sheer force on the at least one tine, while the bulk and thickness of the sphincter resists penetration of the wall of lumen 12 with the tine(s) where intraluminal content could escape outside of the lumen where infection could ensue. This may be accomplished by the angle α between each tine 16 and the central axis of body 14 being between approximately 5 degrees and approximately 45 degrees, such as between approximately 5 degrees and approximately 30 degrees and illustrated as approximately 10 degrees outwardly.

While one tine 16 may be sufficient to resist distal migration of body 14, at least two tines 16 that are axially spaced around body 14 with respect to lumen 12 enhances and more evenly distributes the forces resisting peristalsis. In the illustrated embodiment, each tine 16 is between approximately 0.5 cm and approximately 2.0 cm. In this manner, even with proximate/distal movement of body 14 in response to peristalsis of lumen 12, any commensurate movement of the tine(s) 16 within the sphincter, will not cause the tine(s) to disengage from the sphincter. If a plurality of tines 16 are used they may be of different lengths to provide a variety of engagements with the sphincter.

Figure 3:
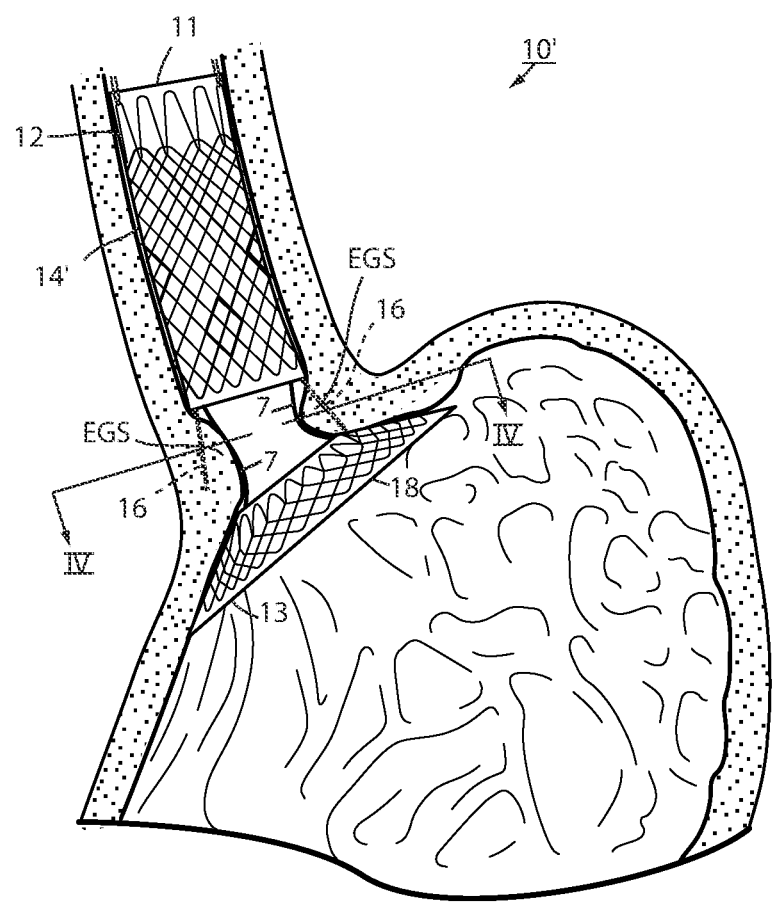
FIG. 3 is the save view as FIG. 2 of an alternative embodiment of an intraluminal device having a body, another body and a connector connecting the bodies position at the esophageal-gastric sphincter of the recipient.
Figure 4:
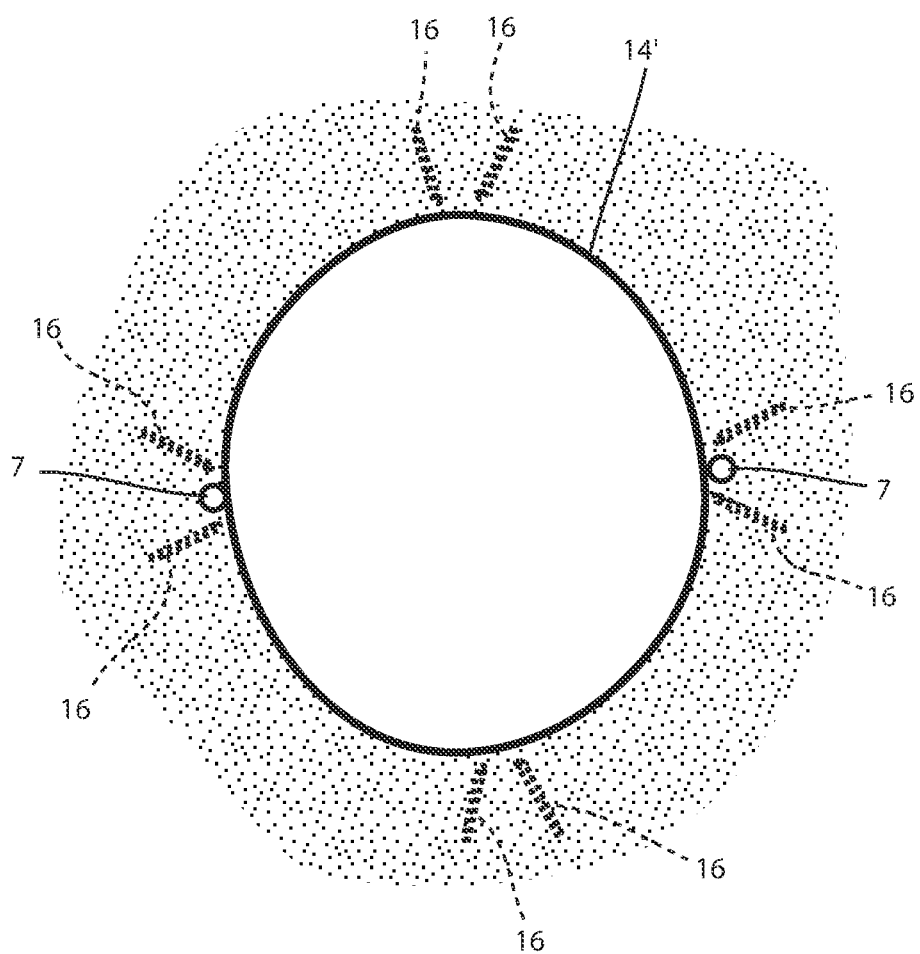
FIG. 4 is a sectional view taken along the lines IV-IV in FIG. 3.

In the illustrated embodiment in FIG. 3, device 10' body 14' is coupled with another body 18 with a connector 7. With intraluminal device 10' deployed at lumen 12 with body 14' proximal the sphincter and tine(s) 16 penetrating the EG sphincter, another body 18 is distal of the sphincter and connector 7 connecting body 14' with another body 18 passing through the EG sphincter. Connector 7 is configured to not substantially interfere with operation of the sphincter while passing through the sphincter. FIG. 4 illustrates a possible arrangement of a plurality of tines 16 disposed angularly around the distal end of body 14'. As can be seen, two tines 16 angle radially away from each connector 20 and two tines angle radially away from each other offset from the connectors. Other arrangements are possible.

Intraluminal device 10' may be deployed with a deployment device of the type disclosed in commonly assigned U.S. Pat. No. 9,545,326, the disclosure of which is hereby incorporated herein by reference. Deployment begins by compressing body 14' and another body 18 and positioning them in the deployment device along with connector 7. The deployment device is deployed in the lumen 12 at least partially distal of the EG sphincter using techniques disclosed in the '326 patent. Another body 18 is deployed from the deployment device distal of the EG sphincter. The deployment device is then pulled proximally and body 14' and at least one tine 16 is deployed from the deployment device in a position that is proximal the muscle of the EG sphincter. After body 14' is deployed from the deployment device, distal movement of the body will result in the at least one tine 16 penetrating the muscle of the EG sphincter.

Figure 5:
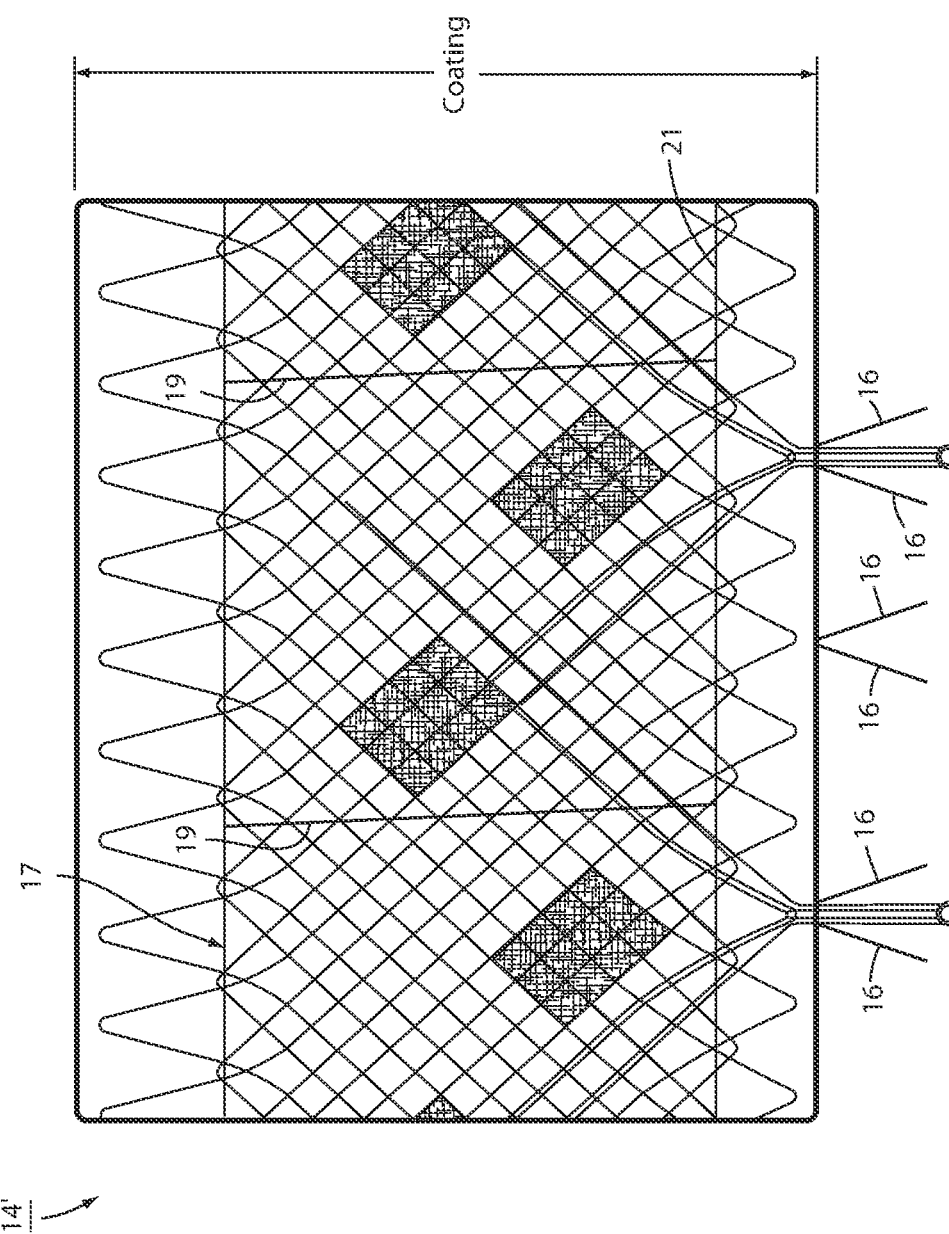
FIG. 5 is a flattened view of the body in FIG. 3 illustrating interview details thereof.

Intraluminal device 10' may be explanted with an endoscopic grasper or hook pulling proximally on a removal ring 17. In the illustrated embodiment, removal ring 17 is made of a suture or other material weaving between proximal ends of the support mesh of body 14' (FIG. 5). This distributes the proximal force evenly around the perimeter of body 14' and pulls the wall inward from the esophagus thus reducing any tendency to injure the esophagus. One or more force transfer sutures 19 transfers the movement of removal ring 17 to a retraction ring 21. Retraction ring 21 retracts tines 16 inwardly in order to reduce any scratching of the tine tips along the esophagus as body 14' is removed. Retraction ring 21 functions by applying an inward force on a distal end of body 14', by applying an inward force directly on the tines 16 or by retracting the tines into pockets provided in body 14'. Other methods will be apparent to the skilled artisan.

For intraluminal device 10', body 14' is an esophageal member 11 configured to the size and shape of the distal portion of the esophagus and another body 18 is a cardiac member 13 that is configured to the size and shape of a portion of the cardiac portion of the stomach as illustrated in FIG. 3. Connector 7 passes through the esophageal-gastric (EG) sphincter. Such embodiment is useful as a bariatric device and method as disclosed in commonly assigned international application publication WO 2016/109346 or a metabolic disease treatment device and method as disclosed in commonly assigned international application publication WO 2015/031077 the disclosures of which are hereby incorporated herein by reference. In order to function as a bariatric device or a metabolic disease treatment device, cardiac member 13 applies pressure to the cardiac portion of the stomach at least part of the time via connector 7 being under tension. In order to do so, while allowing esophageal member 11 to be initially deployed sufficiently proximal of the EG sphincter to allow the distal tip of tine(s) 16 to engage the muscle of the EG sphincter, connector 7 and/or cardiac member 13 may be sufficiently flexible in order to accommodate temporary further spacing between the esophageal member and the cardiac member while maintaining position of the cardiac member 13 generally distal of the EG sphincter. This may be accomplished by connector 7 being elastic and/or by cardiac member 13 being flexible. In that manner, the connector and/or cardiac member can flex to allow tine(s) 16 to engage the EG sphincter then relax sufficiently to place pressure on the cardiac portion of the stomach.

Figure 6:
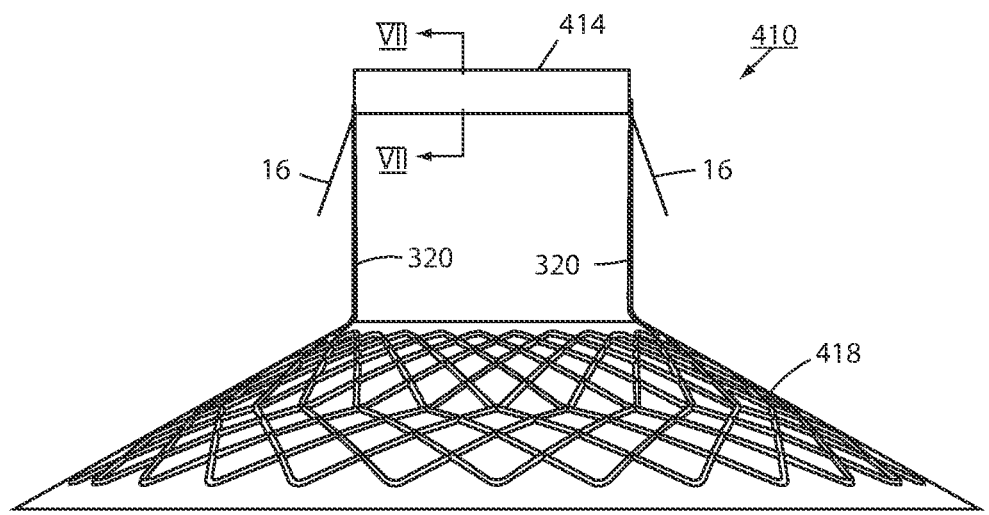
FIG. 6 is a side elevation of an alternative embodiment of an intraluminal device adapted to be positioned at the esophageal-gastric sphincter of the recipient.
Figure 7:
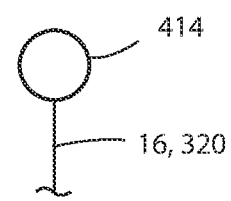
FIG. 7 is a sectional view taken along the lines VII-VII in FIG. 6.

In another embodiment illustrated in FIG. 6 an intraluminal device 410 has a body 414 that is configured to be positioned at a distal portion of the esophagus, another body 418 that is configured to be positioned against the cardiac portion of the stomach and a connector 320 that passes through the esophageal-gastric sphincter in a manner that does not interfere with operation of the EG sphincter. Body 414 is ring-shaped in order to pass intraluminal content through the esophagus and, as can best be seen in FIG. 7, body 414 has a curvilineal cross section in order to minimize any potential irritation of the esophagus.

Tine(s) 16 can be made of nitinol wire, stainless steel, titanium, carbon fiber, or the like, covered with a biocompatible material such as a silicone coating. This makes the tine(s) stiff yet flexible. Each tine is directed generally distally but with an outward slant. This ensures that the tine engages the sphincter. Each tine is directed more distally than outwardly so that shear forces on the tine are minimal. Also this minimizes possibility of the tine penetrating the wall of lumen 12. For example, the angle between each tine and the central axis of body 314 may be between approximately 5 degrees and approximately 45 degrees but a greater or lesser amount may be used such as between approximately 5 degrees and approximately 30 degrees or approximately 10 degrees. An enlarged tip 26 of tine(s) 16 may be provided to resist catching on a deployment device or other surface. Although two tines 16 are shown, one on each side of body 414, more than two tines may be used. A plurality of additional distally directed tines may be deployed, each between one of the ones shown and body 418.

An intraluminal device 20 (FIG. 8) is adapted to be deployed in a lumen 22, such as the esophagus that experiences peristaltic waves and has muscle defining an intraluminal sphincter, such as the lower esophageal sphincter (LES) also known as the esophageal gastric sphincter (EGS). Intraluminal device 20 includes a body 24 having a size and shape of a portion of the lumen proximal of the sphincter and one or more anchors 25 extending from body 24 and adapted to resist distal migration of body 24.

Body 24 includes an esophageal member 30 having a size and shape of a portion of the distal portion of the esophagus and a cardiac member 32 having a size and shape of the cardiac portion of the stomach coupled with esophageal member 30 with a connector 34. Connector 34 in the illustrated embodiment is a pair of tension members, or struts, connecting esophageal member 20 and cardiac member 32, but other configurations are possible. Connector 34 causes cardiac member 32 to apply stress to the cardiac portion of the stomach when connector 32 passes through the EG sphincter. Anchor(s) 25 extend distally from esophageal member 30 resist distal migration of the esophageal member. Each anchor 25 has a base 26 extending distally from esophageal member and one or more tines 27 extending distally from base 26. Each tine may extend directly distally from base 26 or be at a slight angle therefrom. Base 26 positions tine(s) 27 to penetrate the muscle of the esophageal-gastric (EG) sphincter when the esophageal member 30 is deployed in the esophagus upstream of the EG sphincter. Intraluminal device 20 may be deployed in the manner disclosed in International Publication No. WO 2020/194189 A1, the disclosure of which is hereby incorporated herein by reference in its entity, which causes tine(s) 27 of anchor(s) 25 to penetrate the muscle of the EG sphincter.

Figure 8:
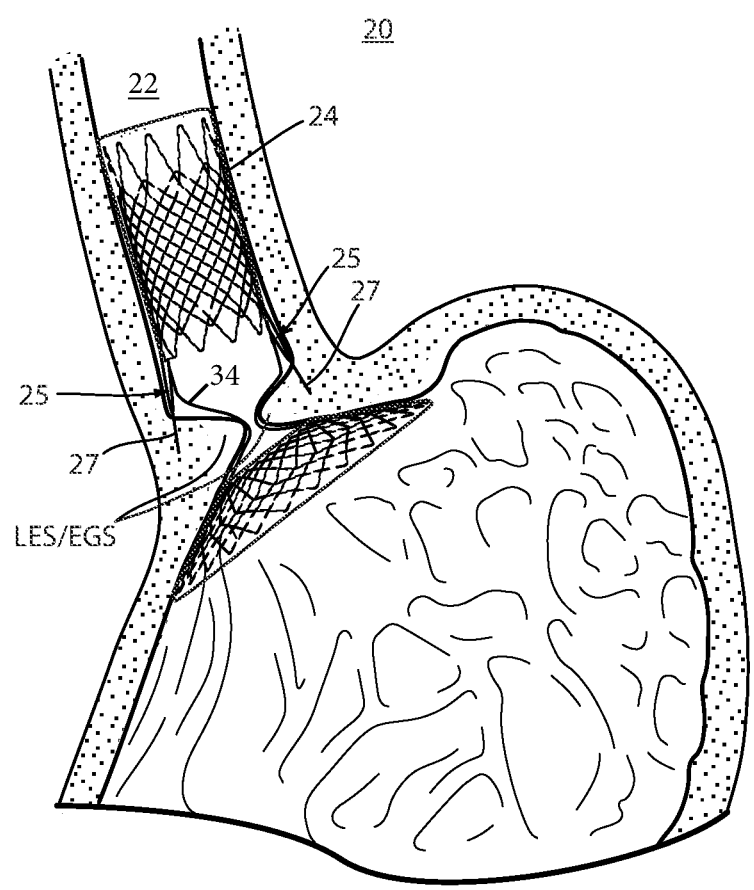
FIG. 8 is a sectional view of the gastro-esophageal region of a patient with an intraluminal device according to an embodiment of the invention deployed therein.
Figure 9:
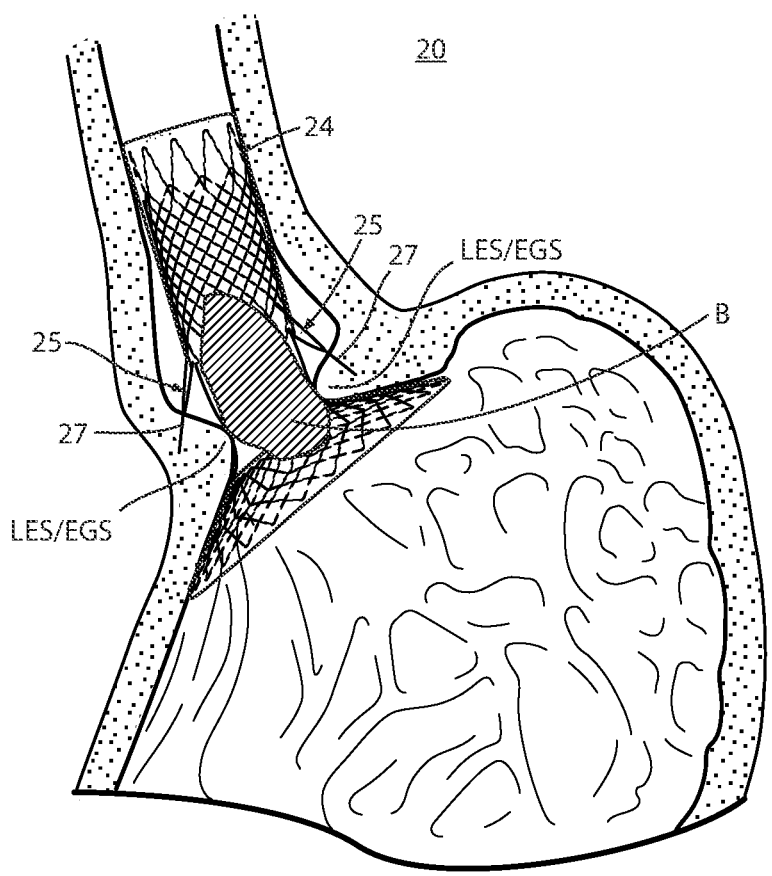
FIG. 9 is the same view as FIG. 8 showing the lower esophageal sphincter (LES) of the esopho-gastric junction (EGJ) opened to pass a bolus of food.

Base 26 is sufficiently stiff so as to be resistant to compression but connected with esophageal member 30 in a manner that allows lateral motion of the tine(s) 27 with respect to esophageal member 30 as seen by comparing FIG. 8 with the EGS closed and FIG. 9 with the EGS opened by peristalsis to pass a bolus of food B. In this manner, with tine(s) 27 penetrating the esophageal gastric sphincter (EGS), aka lower esophageal sphincter (LES), the stiffness of base 26 will transmit any force applied to anchor 25 by peristalsis acting on esophageal member 30 to the LES/EGS which will counteract the distal force applied to the esophageal member. Anchor(s) 25 will therefore resist distal migration of esophageal member 30 yet respond to operation of the LES/EGS by passively following changes in the diameter of the LES during peristalsis. This can best be understood by a comparison of FIGS. 8 and 9. In FIG. 8 intraluminal device 20 has been deployed and the LES is closed. FIG. 9 illustrates peristalsis of the esophagus opening the LES in response to a bolus of food B passing from the esophagus to the stomach. This opening of the LES is accommodated by each anchor 25 passively moving laterally along with opening and closing of the LES muscle. This lateral motion of the tine(s) is accomplished by a hinge-like connection 36 between base 26 and the wall of esophageal member 30 which pivotally mounts the base to the esophageal member. However the generally distal orientation of anchor 25 along with the compression resistance of base 26 continues to resist distal migration of intraluminal device 20 while passively following the diameter of the LES during peristalsis.

Figure 10:
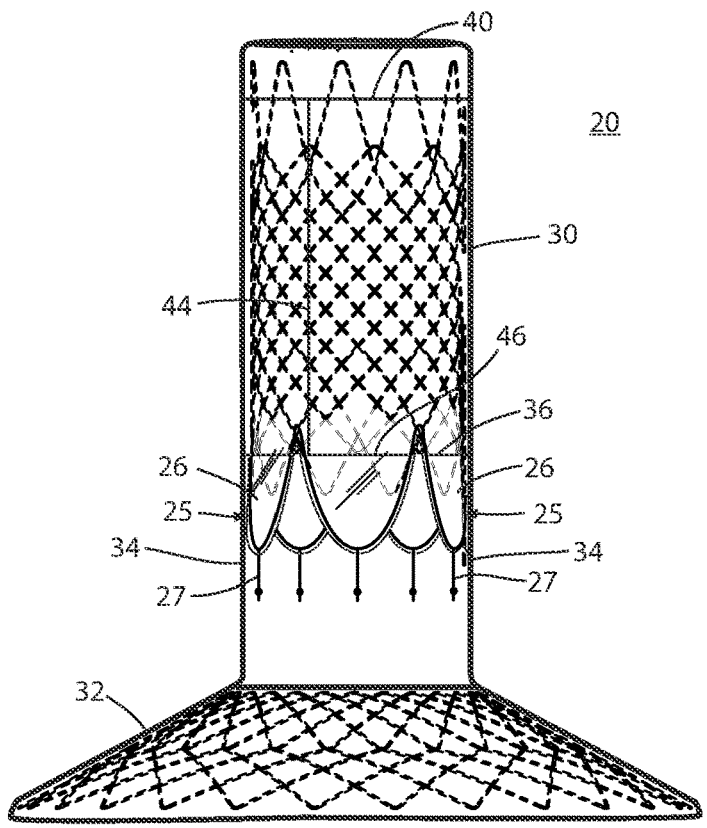
FIG. 10 is a perspective view of the intraluminal device in the posture of FIG. 8.
Figure 11:
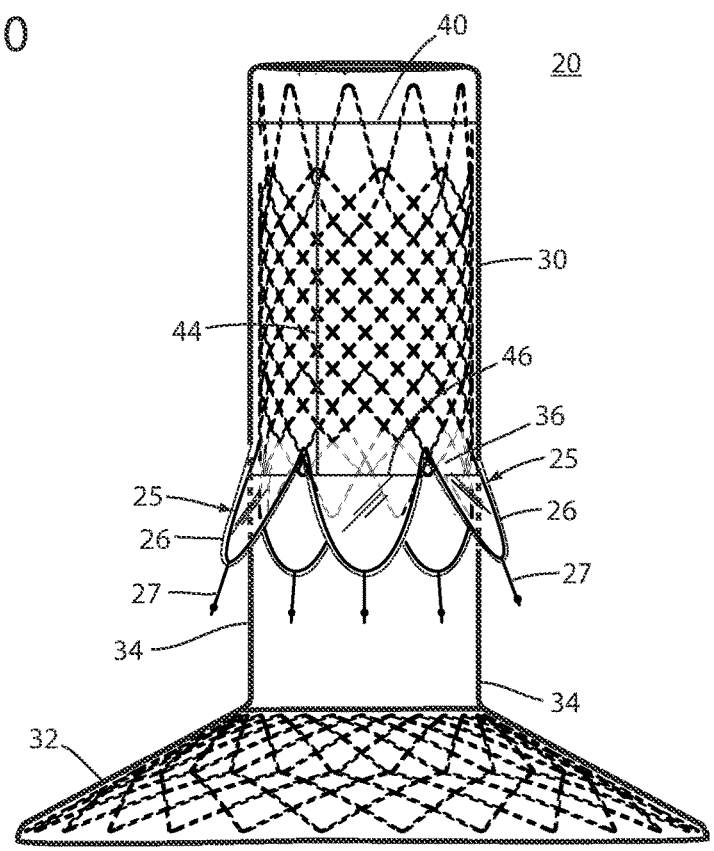
FIG. 11 is a perspective view of the intraluminal device in the posture of FIG. 9.
Figure 12:
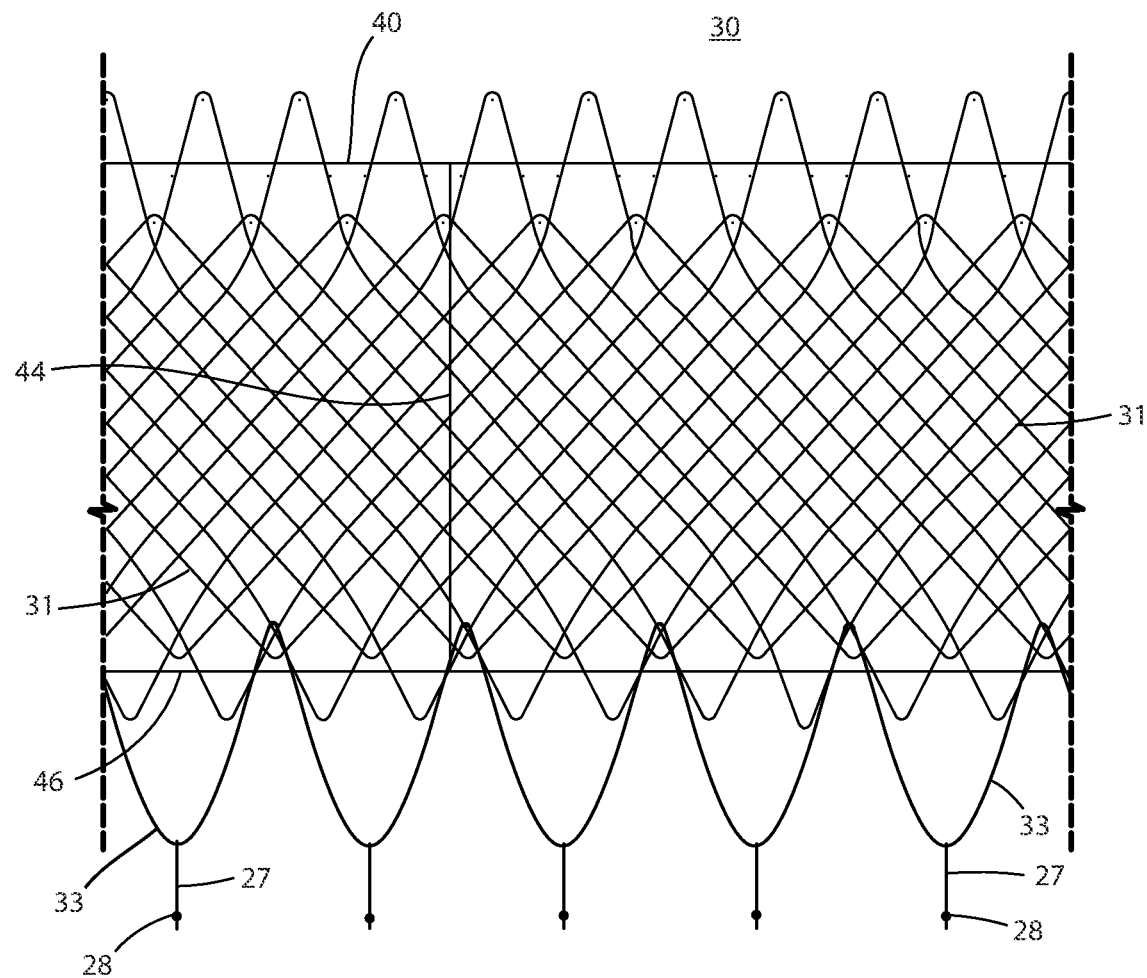
FIG. 12 is a plan view of the mesh supporting structure in FIGS. 8-11 that has been flattened to show details thereof.
Figure 13:
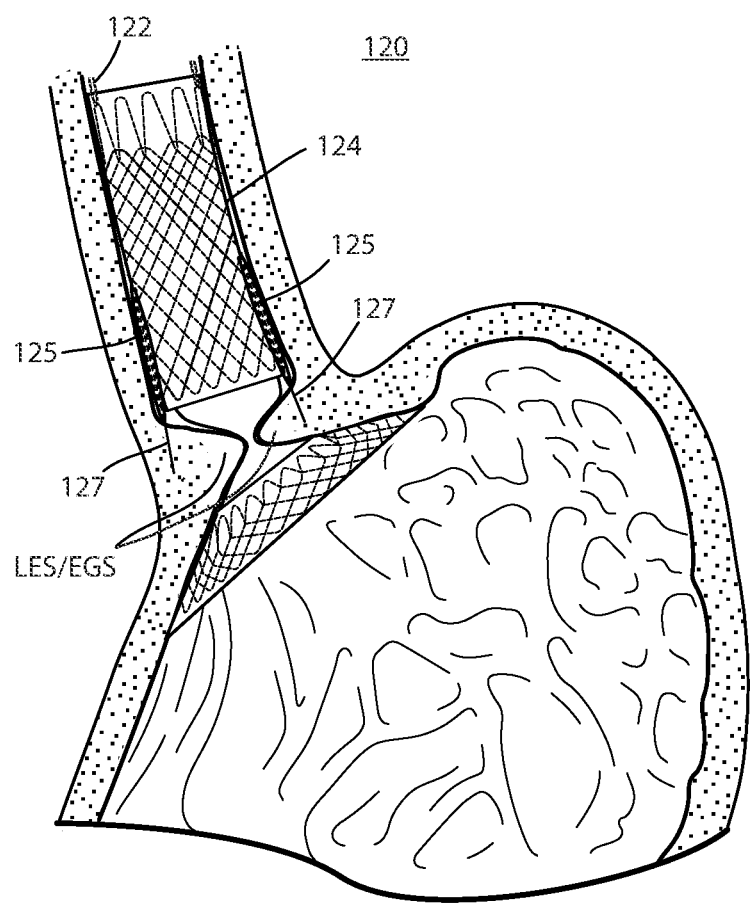
FIG. 13 is the same view as FIG. 8 of an alternative embodiment thereof.
Figure 14:
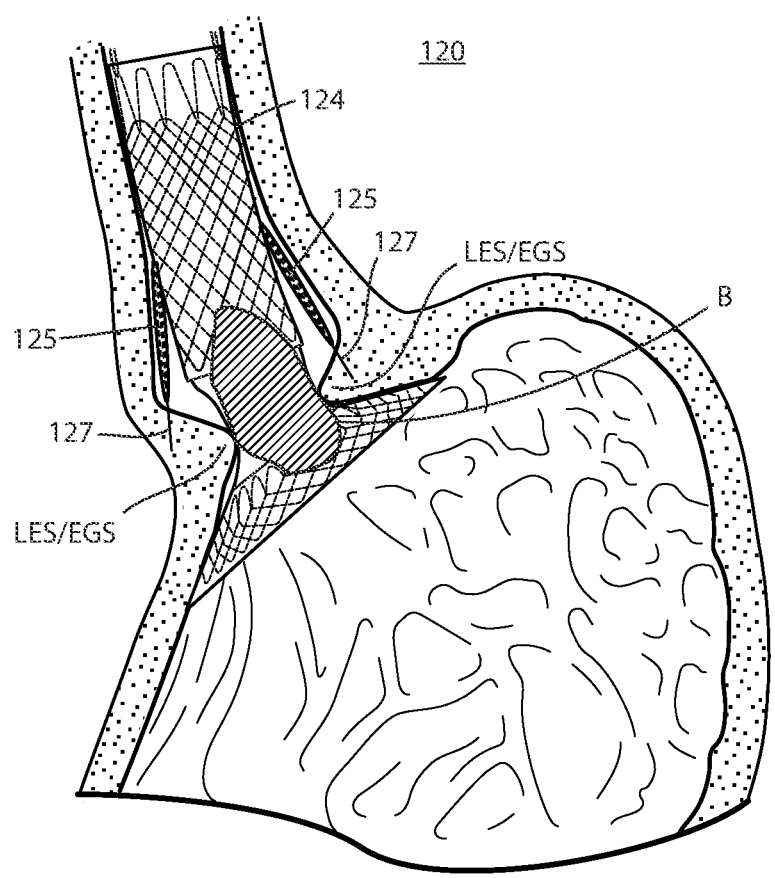
FIG. 14 is the same view as FIG. 9 of the alternative embodiment in FIG. 13.
Figure 15:
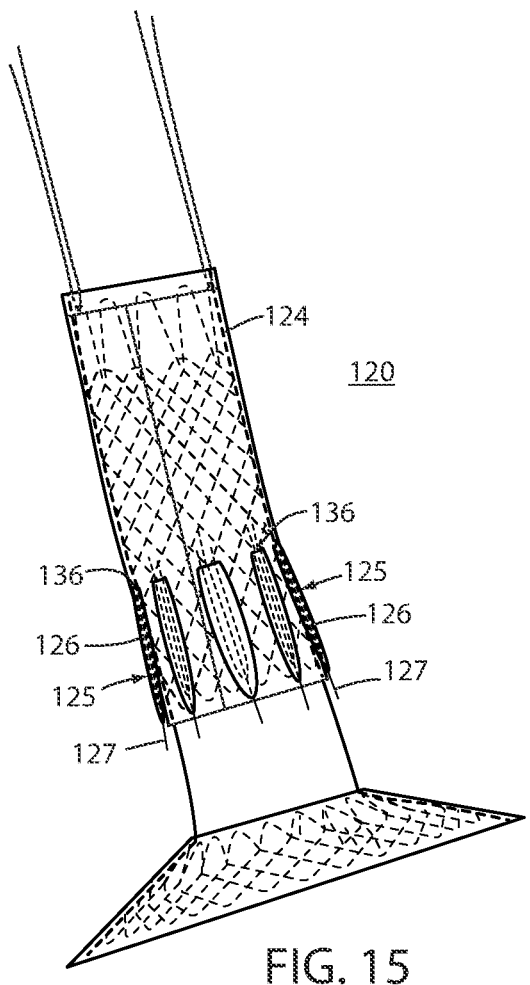
FIG. 15 is a perspective view of the intraluminal device in the posture of FIG. 13.
Figure 16:
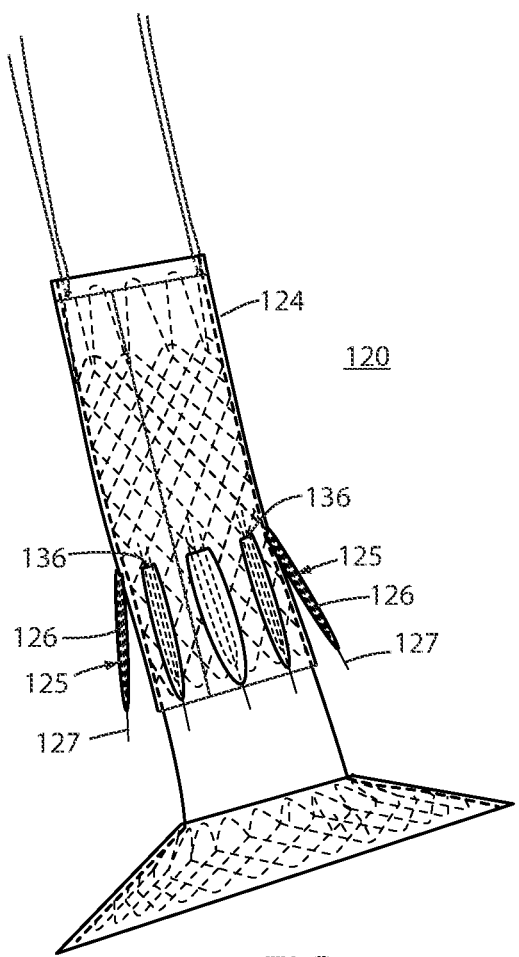
FIG. 16 is a perspective view of the intraluminal device in the posture of FIG. 14.

As best seen in FIGS. 10-12, esophageal member 30 is generally cylindrical of the diameter of the distal esophagus and defined by a support structure made up of a woven mesh 31 formed of an elongated member 31. In the embodiment illustrated in FIGS. 10-12, mesh 31 includes distal extensions 33 which are woven together with mesh 31 and may be either a separate strand of filament or an extension of the filament that forms mesh 31. Each distal extension 33 is a loop which provides structure to a base 26 with one more tines 27 attached to a distal portion of the extension. Esophageal member 30 additionally includes one or more coatings of a biocompatible material, such as silicone, over mesh 31 and extensions 33. The coatings may be continuous thereby defining a tubular member or may have one or more openings therein. In the illustrated embodiment, the material defining mesh 31 and extensions 33 is a metal such as nitinol which is resistant to compression yet allows lateral flexing without metal fatigue. These characteristics of nitinol provide the functionality of anchors 25, namely resistant to compression yet attached to the esophageal member with a hinge-like connection. Since the biocompatible coating is flexible, it allows the extensions 33 to pivot with respect to mesh 31.

Esophageal member 30 has a proximal removal ring 40 interwoven with mesh 31. In order to explant esophageal member 30, the physician snares removal ring with a hook-like member and retracts the removal ring. This will result in a decrease in the diameter of mesh 31 and hence the proximal esophageal member to allow the proximal esophageal member to clear the esophagus and be removed proximally. Esophageal member 30 additionally has a distal retraction ring 46 which performs a similar function as removal ring 40 but to the distal portion of the esophageal member and a transfer suture 44 which interconnects removal ring 40 and retraction ring 46. Thus when the physician retracts removal ring 40, the force is transferred by transfer suture 44 to retraction ring 46 which also retracts and shrinks the distal diameter of the esophageal member. This reduction in diameter distally to the esophageal member 30 retracts anchors 25 inwardly away from the esophageal wall so that tines 27 do not score the esophageal wall as the esophageal member is removed.

In the illustrated embodiment, a plurality of anchors 25 are distributed equally around a perimeter of esophageal member 30. Each tine 27 has a length sufficient to penetrate to the muscularis of the lower esophageal sphincter without penetrating outside of the lumen of the gastrointestinal tract. This penetration is sufficient to prevent the tine from separation from the LES yet avoids potential infections from the microbes in the GI tract entering the abdominal cavity. In the illustrated embodiment, times 27 have a sufficient length to penetrate the muscularis of the LES to further stabilize intraluminal device 20. Tines 27 may have an enlarged diameter 28 in order to resist withdrawal of the tine from the muscle of the LES. With time, tissue of the LES will grow around the enlarged diameter 28 in order assist in resisting withdrawal. As seen best in FIG. 12, the enlarged diameter 28 may be in a distally directed arrowhead shape to allow insertion of the tine in the muscle while resist withdrawal. However other shapes are possible such as a ball-shape in FIG. 20 or double ball shape in FIG. 22. Also a double arrowhead shape of the enlarged diameter may be used as shown in FIG. 21.

Figure 17:
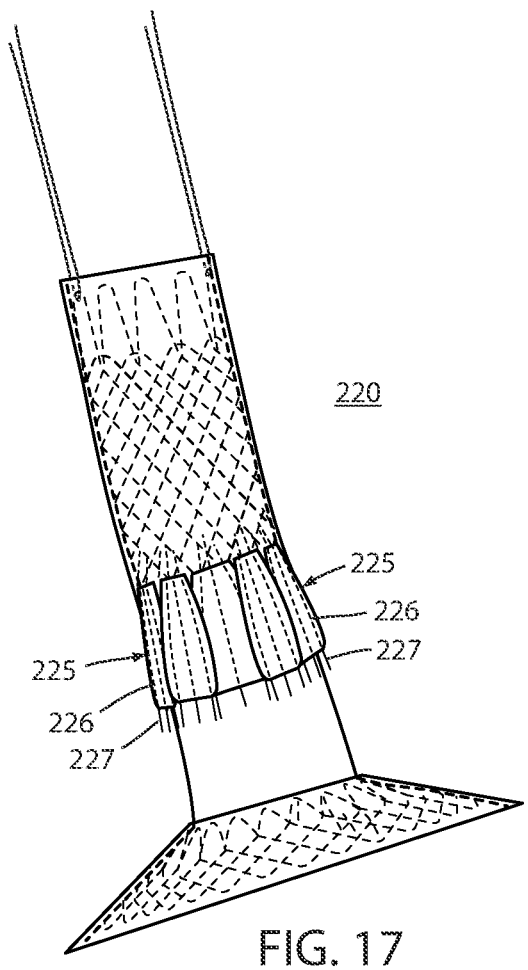
FIG. 17 is the same view as FIG. 10 of another alternative embodiment thereof.
Figure 18:
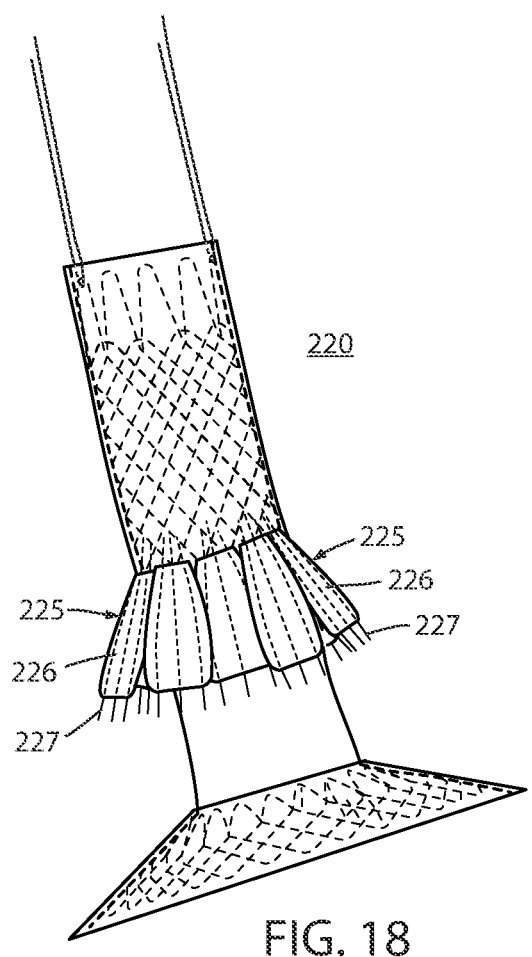
FIG. 18 is the same view as FIG. 11 of the another alternative embodiment in FIG. 17.
Figure 19:
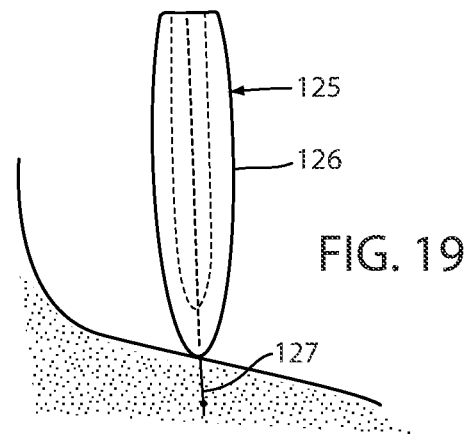
FIG. 19 is an enlarged view of an anchor showing details thereof.

In an alternative embodiment of an intraluminal device 120 shown in FIGS. 13 through 16, anchors 125 are connected with a hinge line connection 136 at a more proximal portion of esophageal member 30. Bases 126 of anchors 125 are longer than bases 26 of anchors 25 in order to position each tine 127 at the LES with intraluminal device 125 deployed. In another alternative embodiment of an intraluminal device 220 shown in FIGS. 17 and 18 anchors 225 are peddle shaped so that as the tines 227 move laterally passively under the opening (FIG. 18) and closing (FIG. 17) action of the LES, the bases 226 or the anchors 225 overlap each other as best seen in FIG. 17. Other embodiments will suggest themselves to the skilled artisan.

Figure 20:
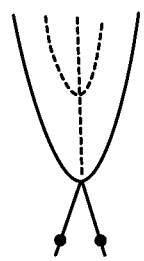
FIG. 20 is the same view as FIG. 19 of an alternative embodiment thereof.
Figure 21:
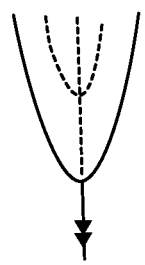
FIG. 21 is the same view as FIG. 19 of another alternative embodiment thereof.
Figure 22:
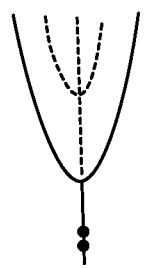
FIG. 22 is the same view as FIG. 19 of yet another alternative embodiment thereof.
Figure 23:
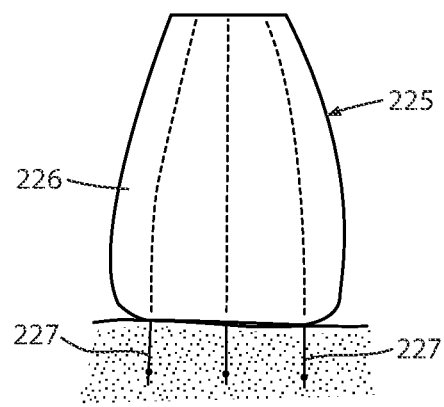
FIG. 23 is the same view as FIG. 19 of an embodiment having multiple tines.

Variations in anchor configuration are shown in FIGS. 20 through 23. In FIG. 20, at least two tines are used that are angular with respect to each other. In FIG. 21 the enlarged diameter of the tine is a multiple arrowhead configuration and in FIG. 22 multiple spheres. In FIG. 23 multiple tines are provide, each supported by a separate strand of the filament defining the mesh.

Deployment of intraluminal device 20 begins by compressing body 24 and positioning it in a deployment device of the type disclosed in commonly assigned U.S. Pat. No. 9,545,326, the disclosure of which is hereby incorporated herein by reference. The deployment device is deployed in the lumen 22 at least partially distal of the LES using techniques disclosed in the '326 patent. Cardiac member 32 is deployed from the deployment device in the stomach. The deployment device is then pulled proximally to position the cardiac member against the upper portion (cardia) of the stomach and at least partially deploying esophageal member 30 into the esophagus proximal the LES. With further proximal force applied to the deployment device, esophageal member 30 is then fully deployed from the deployment device with the tines 27 proximal of the LES. Distal movement of body 24 from peristalsis will result in the tines 27 penetrating the muscle of the LES as seen in FIG. 8. With tines 27 penetrating the LES, distal migration of intraluminal device 20 will be resisted and normal functioning of the LES will be accommodated as anchors 25 follow the diameter of the LES during operation While the foregoing description describes several embodiments of the present invention, it will be understood by those skilled in the art that variations and modifications to these embodiments may be made without departing from the spirit and scope of the invention, as defined in the claims below. The present invention encompasses all combinations of various embodiments or aspects of the invention described herein. It is understood that any and all embodiments of the present invention may be taken in conjunction with any other embodiment to describe additional embodiments of the present invention. Furthermore, any elements of an embodiment may be combined with any and all other elements of any of the embodiments to describe additional embodiments.

The embodiments of the invention in which an exclusive property or privilege is claimed are defined as follows:

1. A method of resisting migration of a device in a lumen, said lumen having an esophagus, a stomach and a muscle defining a gastro-esophageal (EG) sphincter between the esophagus and the stomach, said method comprising:
    said device having a body with a size and shape of a portion of the lumen wherein said device body is coupled with another body with a connector, wherein said body comprises an esophageal member configured to the size and shape of the distal portion of the esophagus wherein said another body comprises a cardiac member distal of the gastro-esophageal (EG) sphincter, and configured to the size and shape of a portion of the cardiac portion of the stomach wherein said connector passes through the EG sphincter
    the device further includes at least one tine extending distally from the body, said at least one tine being rigid or semi rigid, wherein said at least one tine is configured to penetrate the muscle of the EG sphincter sufficiently to resist separation of the at least one tine from the muscle due to peristalsis;
    deploying the device in the lumen with the body proximal the EG sphincter with respect to peristaltic movement of the lumen with the at least one tine penetrating the muscle of the sphincter; and
    explanting the device including moving the at least one tine to not extend outwardly from the body, wherein said device includes a removal ring at a proximal end portion of the body and a retraction ring at a distal end portion of the body that is connected with said removal ring wherein proximal force applied to said removal ring causes said retraction ring to move the at least one tine inwardly.

2. The method as claimed in claim 1 wherein said at least one tine comprises at least two tines that are axially spaced around the body with respect to the lumen.

3. The method as claimed in claim 1 wherein said deploying the device comprises (i) compressing the body and the another body in a deployment device, (ii) positioning the deployment device at least partially distal of the EG sphincter and deploying the another body from the deployment device distal of the EG sphincter, (iii) moving the deployment device proximally and deploying the body and the at least one tine proximal of the EG sphincter and (iv) further deploying the device from the deployment device and allowing subsequent movement of the device causing the at least one tine to penetrate the EG sphincter.

4. The method as claimed in claim 3 wherein at least one selected from said connector and said another device is sufficiently flexible in order to perform (iii) while maintaining said another body distal to the EG sphincter.

5. The method as claimed in claim 1 wherein said at least one tine is directed distally and outwardly, but more distally than outwardly.

6. The method as claimed in claim 5 wherein said at least one tine is directed distally and outwardly at angle between said at least one tine and a central axis of said body between approximately 5 degrees and approximately 45 degrees.

7. The method as claimed in claim 1 wherein said at least one tine has a length of between approximately 0.5 cm and approximately 2.0 cm.

8. The method as claimed in claim 1 including an enlarged tip of said at least one tine to resist catching on a surface.

9. The method as claimed in claim 1 wherein said at least one tine is configured to be retained entirely within said lumen.

10. The method as claimed in claim 1 wherein said traction ring moves said at least one tine inwardly by at least one selected from (i) reducing a diameter of said distal end portion of said body (ii), pulling inwardly on said at least one tine, and (iii) retracting said at least one tine into a pouch.

11. An intraluminal device that is adapted to be deployed in a lumen that experiences peristaltic waves and has muscle defining an esophageal-gastric (EC)-sphincter, said intraluminal device comprising:
    an esophageal member having a size and shape of a portion of the distal portion of the esophagus and at least one anchor extending distally from the esophageal member and adapted to resist distal migration of said esophageal member; and
    said at least one anchor comprising a base extending distally from the esophageal member and at least one tine extending distally from the base, said base adapted to position said at least one tine to penetrate the muscle of the esophageal-gastric (EG) sphincter when the esophageal member is deployed in the esophagus upstream of the EG sphincter and said base adapted to allow lateral motion of the tine with respect to said esophageal member; and a cardiac member having a size and shape of the cardiac portion of the stomach coupled with said esophageal member with a connector, said connector configured to cause said cardiac member to apply stress to the cardiac portion of the stomach when said connector passes through the EG sphincter and said cardiac member is in the stomach; and
    wherein said esophageal member comprises a mesh and a flexible cover over said mesh and wherein said base comprises an extension of said mesh and said flexible cover.

12. The intraluminal device as claimed in claim 11 wherein said at least one anchor comprises a plurality of said anchors distributed around a perimeter of said esophageal member.

13. The intraluminal device as claimed in claim 11 wherein said at least one tine has a length sufficient to penetrate to the muscularis of the EG sphincter without penetrating outside of the lumen.

14. The intraluminal device as claimed in claim 11 wherein said at least one tine comprises at least two tines.

15. The intraluminal device as claimed in claim 14 wherein said at least two tines are angular at an angle with respect to each other.

16. The intraluminal device as claimed in claim 11 including an enlarged diameter of said at least one tine that is adapted to resist withdrawal of said at least one tine from the muscle of the EG sphincter.

17. The intraluminal device as claimed in claim 16 wherein said enlarged diameter is shaped as a sphere or a triangle.

18. The intraluminal device as claimed in claim 11 wherein said mesh comprises a metal.

19. The intraluminal device as claimed in claim 18 wherein said metal comprises nitinol.

20. The intraluminal device as claimed in claim 11 wherein said flexible cover comprises a silicone.

21. A method of resisting distal migration of an intraluminal device that is deployed in a lumen that experiences peristaltic waves and has muscle defining an esophageal-gastric (EG) sphincter, said intraluminal device having an esophageal member having a size and shape of a portion of the distal portion of the esophagus, a cardiac member having a size and shape of the cardiac portion of the stomach coupled with said esophageal member with a connector, said connector configured to cause said cardiac member to apply stress to the cardiac portion of the stomach when said connector passes through the EG sphincter and said cardiac member is in the stomach, said method comprising:
- having at least one anchor extending distally from the esophageal member and adapted to resist distal migration of said esophageal member;
- said at least one anchor comprising a base extending distally from the esophageal member and at least one tine extending distally from the base, and
- said base positioning said at least one tine to penetrate the muscle of the esophageal-gastric (EG) sphincter when the esophageal member is deployed in the esophagus upstream of the EG sphincter and said base allowing lateral motion of the tine with respect to said esophageal member in response to operation of the EG sphincter.

* * * * *

UNITED STATES PATENT AND TRADEMARK OFFICE
CERTIFICATE OF CORRECTION

PATENT NO. : 12,127,958 B2
APPLICATION NO. : 17/484344
DATED : October 29, 2024
INVENTOR(S) : Randal S. Baker and Frederick J. Walburn It is certified that error appears in the above-identified patent and that said Letters Patent is hereby corrected as shown below:

In the Claims

Column 12, Line 62, Claim 15, delete "angular" after "are"

Signed and Sealed this
Tenth Day of December, 2024

Katherine Kelly Vidal
*Director of the United States Patent and Trademark Office*